US010040068B2

United States Patent
Sattler et al.

(10) Patent No.: US 10,040,068 B2
(45) Date of Patent: Aug. 7, 2018

(54) REAGENT VESSEL HOLDER FOR AN ANALYTICAL INSTRUMENT, REAGENT SUPPLY SYSTEM FOR AN ANALYTICAL INSTRUMENT AND AN ANALYTICAL INSTRUMENT

(71) Applicants: Roche Diagnostics Operations, Inc., Indianapolis, IN (US); Hitachi High-Technologies Corporation, Tokyo (JP)

(72) Inventors: Stephan Sattler, Starnberg (DE); Reinhold Kraemer, Peissenberg (DE); Hidenobu Komatsu, Tokyo (JP); Toshio Suzuki, Tokyo (JP)

(73) Assignees: Roche Diagnostics Operations, Inc., Indianapolis, IN (US); Hitachi High-Technologies Corporation, Tokyo (JP)

( * ) Notice: Subject to any disclaimer, the term of this patent is extended or adjusted under 35 U.S.C. 154(b) by 150 days.

(21) Appl. No.: 15/163,039

(22) Filed: May 24, 2016

(65) Prior Publication Data
US 2016/0263576 A1 Sep. 15, 2016

Related U.S. Application Data

(63) Continuation of application No. PCT/EP2014/077368, filed on Dec. 11, 2014.

(30) Foreign Application Priority Data

Dec. 13, 2013 (EP) .................................... 13197125

(51) Int. Cl.
*B01L 9/00* (2006.01)
*B01L 3/00* (2006.01)
(Continued)

(52) U.S. Cl.
CPC ................. *B01L 3/523* (2013.01); *B01L 9/00* (2013.01); *G01N 35/00663* (2013.01);
(Continued)

(58) Field of Classification Search
None
See application file for complete search history.

(56) References Cited

U.S. PATENT DOCUMENTS

| 3,830,425 A | 8/1974 | Stallmann |
| 5,171,538 A | 12/1992 | Tremmel et al. |

(Continued)

FOREIGN PATENT DOCUMENTS

| EP | 1291659 A2 | 3/2003 |
| WO | 2011/105247 A1 | 9/2011 |
| WO | WO-2013165911 A1 * | 11/2013 ............. G01N 35/04 |

OTHER PUBLICATIONS

International Search Report dated Mar. 9, 2015, in Application No. PCT/EP2014/077368, 4 pages.
(Continued)

*Primary Examiner* — Paul S Hyun
(74) *Attorney, Agent, or Firm* — Woodard, Emhardt, Moriarty, McNett & Henry, LLP (57) ABSTRACT

A reagent vessel holder for an analytical instrument is disclosed. The reagent vessel holder comprises at least one reagent vessel compartment for receiving a reagent vessel, wherein the reagent vessel compartment comprises a base and at least two lateral guiding elements, and at least one hollow needle for piercing the reagent vessel. The hollow needle is disposed on a front end of the reagent vessel compartment near the base and extends in a direction substantially parallel to the base. The lateral guiding elements are disposed so as to be adapted to slidably guide the reagent vessel in a direction substantially parallel to the
(Continued)

direction, in which the hollow needle extends. The lateral guiding elements are adapted to receive the reagent vessel therebetween and are biased towards one another. Further, a reagent supply system for an analytical instrument and an analytical instrument comprising such a reagent vessel holder are disclosed.

11 Claims, 6 Drawing Sheets

(51) Int. Cl.
*G01N 35/10* (2006.01)
*G01N 35/00* (2006.01)

(52) U.S. Cl.
CPC ..... *G01N 35/1002* (2013.01); *G01N 35/1079* (2013.01); *B01L 3/527* (2013.01); *B01L 2200/023* (2013.01); *B01L 2200/025* (2013.01); *B01L 2200/16* (2013.01); *B01L 2300/044* (2013.01); *B01L 2300/045* (2013.01); *B01L 2300/0672* (2013.01); *G01N 2035/00673* (2013.01)

(56) References Cited

U.S. PATENT DOCUMENTS

| | | |
|---|---|---|
| 6,274,092 B1 | 8/2001 | Itoh |
| 7,485,264 B2 | 2/2009 | Itoh |
| 7,790,114 B2 | 9/2010 | Fukuda et al. |
| 2005/0207945 A1 | 9/2005 | Itoh |

OTHER PUBLICATIONS

Sigma-Aldrich, Laboratory Clamps and Supports Benchclamps Brochure, http://www.sigmaaldrich.com/content/dam/sigma-aldrich/docs/Sigma-Aldrich/Brochure/1/laboratory-clamps-and-supports.pdf, 2012, retrieved Apr. 28, 2014, 16 pages.

* cited by examiner

REAGENT VESSEL HOLDER FOR AN ANALYTICAL INSTRUMENT, REAGENT SUPPLY SYSTEM FOR AN ANALYTICAL INSTRUMENT AND AN ANALYTICAL INSTRUMENT

CROSS-REFERENCE TO RELATED APPLICATIONS

This application is a continuation of PCT/EP2014/077368 filed Dec. 11, 2014, which is based on and claims priority to EP 13197125.1 filed Dec. 13, 2013, all of which are hereby incorporated by reference.

BACKGROUND

The present disclosure relates to a reagent holder for an analytical instrument, a reagent supply system for an analytical instrument and an analytical instrument.

Analytical instruments and more particularly medical analytical instruments can serve to examine body fluids, especially blood. Modern instruments of this kind are largely fully automatic in operation, only the samples still having to be inserted in appropriate sample vessels and the desired analysis entered.

The present disclosure is intended for instruments which operate with liquid reagents contained in reagent vessels made of plastic. The instruments usually have a cooled reagent space. The reagents are transported in the instrument from the reagent vessels to the reaction vessels and there mixed with the sample and, after completion of the reaction, a physically detectable change is measured as a measure of the analysis. The measurement may be based on a coloring or an electrochemical detection. The reagent vessels are frequently specially adapted to the reagent space of a particular instrument. By this, space-saving accommodation and effective cooling of the reagents is possible. Reagent vessels and the reagent space of the instrument belonging to them, if they are functionally adapted to each other, form a system called a reagent supply system. Alternatively, the reagent vessel may comprise a system reagent such as a cleaning liquid for cleaning the instrument. Such system reagents are not cooled.

For the transport of the reagents from the reagent vessel into the reaction vessel, essentially two basically different techniques are used, namely the pipetting technique and the dispenser technique.

In the pipetting technique, a pipette, usually fastened to a movable arm, dips from above through the open reagent vessel and an appropriate amount of reagent is sucked in and transferred in the pipette (which is also known as a transfer needle) to the reaction vessel. This technique makes it possible to change the reagent vessels easily. A complicated instrument mechanism is however required. Also the transfer of reagents is relatively slow, as a result of which the throughput rate of the instrument is limited.

With the dispenser technique, the reagent vessels are permanently connected individually by a line to the instrument. The connection lines are a part of a line system through which the reagents are supplied in a suitable manner to the reaction vessels and thereby to the analysis. By this means, with relatively little mechanical complication, they are always available. This allows high analysis frequencies and thereby very rapidly operating automatic, analyzers.

The dispenser technique has however considerable disadvantages with regard to handling. Usually, flexible connecting tubes are introduced from above into the reagent vessels so that they end just above the vessel bottom. This is difficult and can easily lead to errors. In particular, it can occur that air is sucked in if the flexible tubes do not dip deeply enough into the reagent. Also when the flexible tubes are interchanged they must each time be washed in cleaning liquid in order to prevent the transfer of reagent, especially if—as is often customary—various reactions are carried out in the same channel of the instrument and accordingly different reagents are led through one flexible tube.

A known reagent supply system for a medical analytical instrument includes a reagent space provided on the instrument and reagent vessels which are received in the reagent space. In the reagent space, at least one reagent vessel compartment with a bottom, lateral guide elements and a top guiding element as well as a front stop are provided. The instrument contains a fluid communication system for connection with the reagent vessel situated in the reagent vessel compartment. On the end face of the reagent vessel compartment, a hollow needle near the bottom surface thereof is disposed and extends in a direction which is parallel to the bottom surface. On its front wall facing the end face, the reagent vessel has a pierceable seal with a pierceable elastic stopper which is pierced by the hollow needle.

Using such a reagent supply system for a medical analytical instrument provides advantages concerning the handling. Nevertheless, there are still some drawbacks. The process of piercing the reagent vessel requires an accurate operation by the operator as otherwise the hollow needle may be damaged or even broken. Further, the reagent vessels comprise different sizes or widths. Thus, some reagent vessels do not fit into the reagent vessel compartments or need high force to be loaded into the vessel compartment. The reason is that even though the reagent vessels fit within the prescribed reagent vessel tolerances, a variation of the width and the height is unavoidable due to the manufacturing process such as extrusion blow molding. Some reagent vessels comprise bulging even in an empty state which is increased after being filled due to the hydrostatic pressure. Such reagent vessels are squeezed in the reagent vessel compartment. For this reason, the reagent vessel holder comprises tolerances in its dimensions for allowing insertion of such reagent vessel. Another reason for the problems is that narrow bottles have a margin/play in the reagent vessel compartment. The play leads to an off-center piercing of the needle. Thus, the piercing is carried out in the thick wall of the septum provided in the bottle which may cause the needle to be broken.

Therefore, there is a need for a reagent vessel holder for an analytical instrument, a reagent supply system for an analytical instrument and an analytical instrument which are easier and more reliably to be handled and allow compensating tolerances of different reagent vessels without deviating from a center piercing of the needle.

SUMMARY

According to the present disclosure, a reagent vessel holder for an analytical instrument is presented. The reagent vessel holder can comprise at least one reagent vessel compartment for receiving a reagent vessel comprising a pierceable seal disposed in a front wall near a bottom of the reagent vessel. The reagent vessel compartment can comprise a base and at least two lateral guiding elements. The reagent vessel holder can also comprise at least one hollow needle for piercing the reagent vessel. The hollow needle can be disposed on the front end of the reagent vessel compartment near the base and can extend in a direction substantially parallel with a deviation of less than 15° to the base. The lateral guiding elements can be disposed so as to be adapted to slidably guide the reagent vessel in a direction substantially parallel to the direction in which the hollow needle extends. The lateral guiding elements can be adapted to receive the reagent vessel therebetween and can be biased towards one another. The lateral guiding elements can be plate springs. Each of the plate springs can be formed so as to comprise two contacting elements for contacting the reagent vessel at two positions and a connecting portion connecting the contacting elements. The connecting portions can be recessed relative to the contacting elements in a direction away from one another.

Accordingly, it is a feature of the embodiments of the present disclosure to provide a reagent vessel holder for an analytical instrument, a reagent supply system for an analytical instrument and an analytical instrument which are easier and more reliably to be handled and allow to compensate tolerances of different reagent vessels without deviating from a center piercing of the needle. Other features of the embodiments of the present disclosure will be apparent in light of the description of the disclosure embodied herein.

BRIEF DESCRIPTION OF THE SEVEREAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

As used in the following, the terms "have", "comprise" or "include" or any arbitrary grammatical variations thereof can be used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

A reagent vessel holder for an analytical instrument is disclosed. The reagent vessel holder can comprise at least one reagent vessel compartment for receiving a reagent vessel, wherein the reagent vessel compartment can comprise a base and at least two lateral guiding elements, and at least one hollow needle for piercing the reagent vessel, wherein the hollow needle can be disposed on a front end of the reagent vessel compartment near the base and extends in a direction substantially parallel to the base, wherein the lateral guiding elements can be disposed so as to be adapted to slidably guide the reagent vessel in a direction substantially can be adapted to receive the reagent vessel therebetween and can be biased towards one another.

As the lateral guiding elements can be disposed so as to be capable to receive a reagent vessel therebetween, the reagent vessel can be guided on two opposing side surfaces thereof when loaded into the reagent vessel compartment. This arrangement can reduce any lateral movement of the reagent vessel. As the lateral guiding elements can be disposed so as to guide a reagent vessel in a direction substantially parallel to the direction in which the hollow needle extends, the reagent vessel can be pierced in a predetermined direction when loaded into the reagent vessel compartment. As the reagent vessel can usually comprise a pierceable seal in a front wall thereof which can be substantially perpendicular to the side walls thereof, the hollow needle can pierce the reagent vessel in a direction which can be substantially perpendicular to the front wall thereof. Thus, this arrangement can ensure that the piercing process can always be carried out in the same manner when a reagent vessel is loaded into the reagent vessel compartment. As the lateral guiding elements can be biased towards one another, they may contact and center the reagent vessel therebetween independent from any tolerances of the width of the reagent vessel. Usually the pierceable seal can comprise an elastomeric stopper with a septum in the center thereof. Thus, this arrangement can allow the hollow needle to pierce the septum independent from any tolerances of the width of the reagent vessel. Accordingly, any off-center piercing of the needle which may cause the needle to be broken can be avoided.

The lateral guiding elements may be disposed near the base. As the hollow needle can also be disposed near the base and the pierceable seal of the reagent vessel can be disposed near the bottom thereof, the lateral guiding elements may reliably guide the reagent vessel towards the hollow needle and the pierceable seal can be pierced in the center thereof.

The lateral guiding elements may be arranged symmetrically with respect to the direction, in which the hollow needle extends. This arrangement for the lateral guiding elements can further ensure that the pierceable seal can be pierced in the center thereof when the reagent vessel is loaded into the reagent vessel compartment.

The lateral guiding elements may comprise identical biasing forces. Due to the identical biasing forces, the reagent vessel can be centered between the lateral guiding elements independent from any tolerances of the width of the reagent vessel. Particularly, any bulging of the reagent vessel may be compensated by the biasing forces.

The lateral guiding elements may comprise biasing forces, which can be adjusted such that the lateral guiding elements can be adapted to center the reagent vessel when the reagent vessel is received by the lateral guiding elements. This arrangement for the lateral guiding elements can ensure that the lateral guiding elements are not only capable to contact the reagent vessel but they can be capable to shift or move the reagent vessel in a lateral direction if necessary such that the reagent vessel is centered between the lateral guiding elements independent from any tolerances of the width of the reagent vessel.

The lateral guiding elements may be plate springs. Accordingly, the reagent vessel may be centered between the lateral guiding elements independent from any tolerances of the width of the reagent vessel by simple and cheap construction.

Each of the plate springs may be formed so as to be adapted to contact the reagent vessel at two positions when the reagent vessel is received by the lateral guiding elements. For example, the plate springs may be formed so as to be adapted to contact the reagent vessel at the side walls near the front wall and near the rear wall. Thus any lateral tilting or deviation of the guiding direction of reagent vessel from the direction in which the hollow needle extends can be avoided as the reagent vessel can be contacted at two locations on each of the opposing side walls thereof.

Each of the plate springs may be formed so as to comprise two contacting elements for contacting the reagent vessel at two positions and a connecting portion connecting the contacting elements. The connecting portions can be recessed relative to the contacting elements in a direction away from one another. This construction of the plate springs can allow the plate springs to contact the reagent vessel with the contacting elements while the connecting portion may be spaced apart from the reagent vessel. Thus, even if the reagent vessel comprises a bulging near the bottom thereof, the guiding of the reagent vessel may not be constrained as the bulging may be disposed within the free portion or space between the contacting elements and the reagent vessel can still be centered between the lateral guiding elements. In other words, this construction can allow compensating for any bulging of the reagent vessel in a horizontal direction, i.e. a direction parallel to the base.

The plate springs may be formed so as to contact the reagent vessel over a predetermined height. This construction can prevent the reagent vessel from tilting in a direction around the direction in which the hollow needle extends.

The plate springs may be formed so as to be elastically deformed to a different extent over the predetermined height. This construction can allow compensating for any bulging of the reagent vessel in a vertical direction, i.e. a direction perpendicular to the base, and the reagent vessel can still be centered between the lateral guiding elements.

The reagent vessel holder may further comprise a needle holder for holding the hollow needle in a stationary position with respect to the reagent vessel compartment. The needle holder and the lateral guiding elements can be integrally formed. Thus, at least one of the mounting or adjusting tolerances of the hollow needle relative to the reagent vessel can be voided which can increase the precision for centering the reagent vessel relative to the hollow needle.

The needle holder and the lateral guiding elements may be at least partially made of plastics or metal. This construction can be simple and may be manufactured in a cost efficient manner.

Alternatively, or additionally, to the constructions above, the lateral guiding elements may comprise contacting elements which can be at least partially spherical. For example, the contacting elements may be hemispherical. This construction can facilitate the introduction of the reagent vessel between the lateral guiding elements as the partial spherical surface thereof can have an effect similar to a funnel or cone converging towards the hollow needle.

The reagent vessel compartment may further comprise upper lateral guiding elements adapted to slidably guide the reagent vessel in a direction substantially parallel to the direction in which the hollow needle extends. The upper lateral guiding elements can be adapted to receive the reagent vessel therebetween and can be disposed at a position away from the base. This construction can reliably prevent the reagent vessel from tilting in a direction around the direction in which the hollow needle extends as the reagent vessel can be guided in a portion near the base and in another portion away from the base.

The reagent vessel compartment may further comprise a cover, which can be disposed at an end of the reagent vessel compartment opposite to the base. The upper lateral guiding elements can be disposed near the cover. This construction can be very effective in preventing the reagent vessel from tilting in a direction around the direction in which the hollow needle extends as the reagent vessel can be guided in a portion near the base and in another portion almost as far as possible away from the base.

The reagent vessel compartment may further comprise a cover, which is disposed at an end of the reagent vessel compartment opposite to the base, and at least one upper guiding element disposed at the cover so as to be adapted to slidably guide the reagent vessel in a direction substantially parallel to the direction in which the hollow needle extends. The upper guiding element can be adapted to contact the reagent vessel at an upper surface thereof. The upper guiding elements can be differentiated from the upper lateral guiding elements as the upper guiding elements contact the reagent vessel at an upper surface thereof, whereas the upper lateral guiding elements contact the reagent vessel at the side walls thereof. The upper guiding element can press the reagent vessel downwards towards the base such that the hollow needle can reliably meet the pierceable seal. This spring like design can serve to accept reagent vessels of different heights. In other words, low and high reagent vessel may be accepted and the hollow needle can meet the center area of the pierceable seal as the reagent vessels are pushed downwards.

The upper guiding element may be adapted to contact the reagent vessel at the upper surface thereof when the reagent vessel contacts the hollow needle and before being pierced thereby. This construction can cause the hollow needle to reliably meet the pierceable seal. Particularly, the plate spring can press the reagent vessel downwards when the hollow needle starts to pierce the reagent vessel.

The upper guiding element may be a plate spring. This construction can be very simple and may be manufactured in a cost efficient manner.

The plate spring may be formed so as to be adapted to contact the reagent vessel at the upper surface thereof at a first position when the reagent vessel contacts the hollow needle and before being pierced thereby and to additionally contact the reagent vessel at the upper surface thereof at a second position when the reagent vessel is pierced by the hollow needle. Thus, the reagent vessel can be reliably pressed downwards by the upper guiding element.

The second position may be closer to the hollow needle than the first position. The upper guiding element may be at least partially made of plastics or metal. Thus, the plate spring can press the reagent vessel downwards along the complete length in which the hollow needle pierces the reagent vessel.

The lateral guiding elements may be formed so as to be adapted to guide the reagent vessel for a length in a direction substantially parallel to the direction in which the hollow needle extends. The length can be greater than an effective length of the hollow needle. The effective length of the hollow needle can be the length by which the hollow needle projects into the reagent vessel compartment from the front end thereof.

The reagent vessel holder may further comprise a plurality of reagent vessel compartments for receiving a plurality of reagent vessels and a plurality of hollow needles. Each of the plurality of hollow needles can be disposed on a front end of each of the plurality of reagent vessel compartments. Thus, the reagent vessel holder may store more than one reagent vessel and each reagent vessel can be pierced by a hollow needle associated therewith.

A reagent supply system for an analytical instrument can comprise such a reagent vessel holder and at least one reagent vessel held by a reagent vessel compartment of the reagent vessel holder. The reagent vessel can comprise a pierceable seal in a front wall thereof adapted to be pierced by the hollow needle.

An analytical instrument can comprise a reagent space for accommodating such a reagent supply system and a reagent communication system for communicating fluid from the reagent vessel. The reagent communication system can comprise a connection adapted to be connected to the hollow needle of the reagent vessel holder for establishing fluid communication with an interior of the reagent vessel such that a reagent contained in the reagent vessel can be withdrawable by the reagent communication system.

The term "substantially" as used herein in connection with a direction can relate to orientations having a deviation of less than 15°, or in one embodiment than 10° or in another embodiment less than 5° of an exact orientation relative to the direction. For example, substantially parallel to a direction means a deviation of less than 15°, or, in one embodiment, less than 10° or in another embodiment less than 5° form an exact parallel orientation relative to the direction.

A basic idea can be to use elastic deformable guiding elements providing a biasing force for centering the reagent vessel when guided towards the hollow needle. Thus, any tolerances in the width of the reagent vessel, which may be caused by bulging or variation caused by the manufacturing process of the reagent vessel, can be compensated and the reagent vessel can reliably meet the hollow needle at the target location such as the septum of the pierceable seal. Further, any damage of the hollow needle can be prevented which may be caused by an off-center piercing or a movement of the reagent vessel not parallel to the direction in which the hollow needle extends. In one embodiment, as the lateral guiding elements are biased towards one another and elastically deformable or moveable, there can be a freedom for bulging of the reagent vessels. This spring like design can serve as safeguard such that even narrow reagent vessels can be guided well and the hollow needle can meet the center area of the pierceable seal.

Summarizing the findings of the present invention, the following embodiments are described:

Embodiment 1

A reagent vessel holder for an analytical instrument can comprise at least one reagent vessel compartment for receiving a reagent vessel. The reagent vessel compartment can comprise a base and at least two lateral guiding elements. The reagent vessel holder can also comprise at least one hollow needle for piercing the reagent vessel. The hollow needle can be disposed on a front end of the reagent vessel compartment near the base and can extend in a direction substantially parallel to the base. The lateral guiding elements can be disposed so as to be adapted to slidably guide the reagent vessel in a direction substantially parallel to the direction in which the hollow needle extends. The lateral guiding elements can be adapted to receive the reagent vessel therebetween and can be biased towards one another.

Embodiment 2

The reagent vessel holder according to the preceding embodiment, wherein the lateral guiding elements can be disposed near the base.

Embodiment 3

The reagent vessel holder according to any preceding embodiment, wherein the lateral guiding elements can be arranged symmetrically with respect to the direction in which the hollow needle extends.

Embodiment 4

The reagent vessel holder according to any preceding embodiment, wherein the lateral guiding elements can comprise identical biasing forces.

Embodiment 5

The reagent vessel holder according to any preceding embodiment, wherein the lateral guiding elements can comprise biasing forces, which can be adjusted such that the lateral guiding elements can be adapted to center the reagent vessel when the reagent vessel is received by the lateral guiding elements.

Embodiment 6

The reagent vessel holder according to any preceding embodiment, wherein the lateral guiding elements can be plate springs.

Embodiment 7

The reagent vessel holder according to the preceding embodiment, wherein each of the plate springs can be formed so as to be adapted to contact the reagent vessel at two positions when the reagent vessel is received by the lateral guiding elements.

Embodiment 8

The reagent vessel holder according to the preceding embodiment, wherein each of the plate springs can be formed so as to comprise two contacting elements for contacting the reagent vessel at two positions and a connecting portion connecting the contacting elements, wherein the connecting portions can be recessed relative to the contacting elements in a direction away from one another.

Embodiment 9

The reagent vessel holder according to any of the three preceding embodiments, wherein the plate springs can be formed so as to contact the reagent vessel over a predetermined height.

Embodiment 10

The reagent vessel holder according to the preceding embodiment, wherein the plate springs can be formed so as to be elastically deformable to a different extent over the predetermined height.

Embodiment 11

The reagent vessel holder according to any preceding embodiment, further comprising a needle holder for holding the hollow needle in a stationary position with respect to the reagent vessel compartment, wherein the needle holder and the lateral guiding elements can be integrally formed.

Embodiment 12

The reagent vessel holder according to the preceding embodiment, wherein the needle holder and the lateral guiding elements can be at least partially made of plastics or metal.

Embodiment 13

The reagent vessel holder according to any one of embodiments 1 to 5, wherein the lateral guiding elements can comprise contacting elements which can be at least partially spherical.

Embodiment 14

The reagent vessel holder according to the preceding embodiment, wherein the contacting elements can be hemispherical.

Embodiment 15

The reagent vessel holder according to any preceding embodiment, wherein the reagent vessel compartment can further comprise upper lateral guiding elements adapted to slidably guide the reagent vessel in a direction substantially parallel to the direction in which the hollow needle extends, wherein the upper lateral guiding elements can be adapted to receive the reagent vessel therebetween and can be disposed at a position away from the base.

Embodiment 16

The reagent vessel holder according to the preceding embodiment, wherein the reagent vessel compartment can further comprise a cover, which can be disposed at an end of the reagent vessel compartment opposite to the base, wherein the upper lateral guiding elements can be disposed near the cover.

Embodiment 17

The reagent vessel holder according to any preceding embodiment, wherein the reagent vessel compartment can further comprise a cover, which can be disposed at an end of the reagent vessel compartment opposite to the base, and at least one upper guiding element disposed at the cover so as to be adapted to slidably guide the reagent vessel in a direction substantially parallel to the direction in which the hollow needle extends, wherein the upper guiding element can be adapted to contact the reagent vessel at an upper surface thereof.

Embodiment 18

The reagent vessel holder according to the preceding embodiment, wherein the upper guiding element can be adapted to contact the reagent vessel at the upper surface thereof when the reagent vessel contacts the hollow needle and before being pierced thereby.

Embodiment 19

The reagent vessel holder according to any of the two preceding embodiments, wherein the upper guiding element can be a plate spring.

Embodiment 20

The reagent vessel holder according to the preceding embodiment, wherein the plate spring can be formed so as to be adapted to contact the reagent vessel at the upper surface thereof at a first position when the reagent vessel contacts the hollow needle and before being pierced thereby and to additionally contact the reagent vessel at the upper surface thereof at a second position when the reagent vessel can be pierced by the hollow needle.

Embodiment 21

The reagent vessel holder according to the preceding embodiment, wherein the first position can be closer to the hollow needle than the second position.

Embodiment 22

The reagent vessel holder according to any of the five preceding embodiments, wherein the upper guiding element can be at least partially made of plastics or metal.

Embodiment 23

The reagent vessel holder according to any preceding embodiment, wherein the lateral guiding elements can be formed so as to be adapted to guide the reagent vessel for a length in a direction substantially parallel to the direction in which the hollow needle extends, wherein the length can be greater than an effective length of the hollow needle.

Embodiment 24

The reagent vessel holder according to any preceding embodiment can further comprise a plurality of reagent vessel compartments for receiving a plurality of reagent vessels and a plurality of hollow needles, wherein each of the plurality of hollow needles can be disposed on a front end of each of the plurality of reagent vessel compartments.

Embodiment 25

A reagent supply system for an analytical instrument, comprising a reagent vessel holder according to any preceding embodiment and at least one reagent vessel held by a reagent vessel compartment of the reagent vessel holder, wherein the reagent vessel can comprise a pierceable seal in a front wall thereof adapted to be pierced by the hollow needle.

Embodiment 26

An analytical instrument, comprising a reagent space for accommodating a reagent supply system according to the preceding embodiment and a reagent communication system for communicating fluid from the reagent vessel, wherein the reagent communication system can comprises a connection adapted to be connected to the hollow needle of the reagent vessel holder for establishing fluid communication with an interior of the reagent vessel such that a reagent contained in the reagent vessel can be withdrawable by the reagent communication system.

Figure 1:
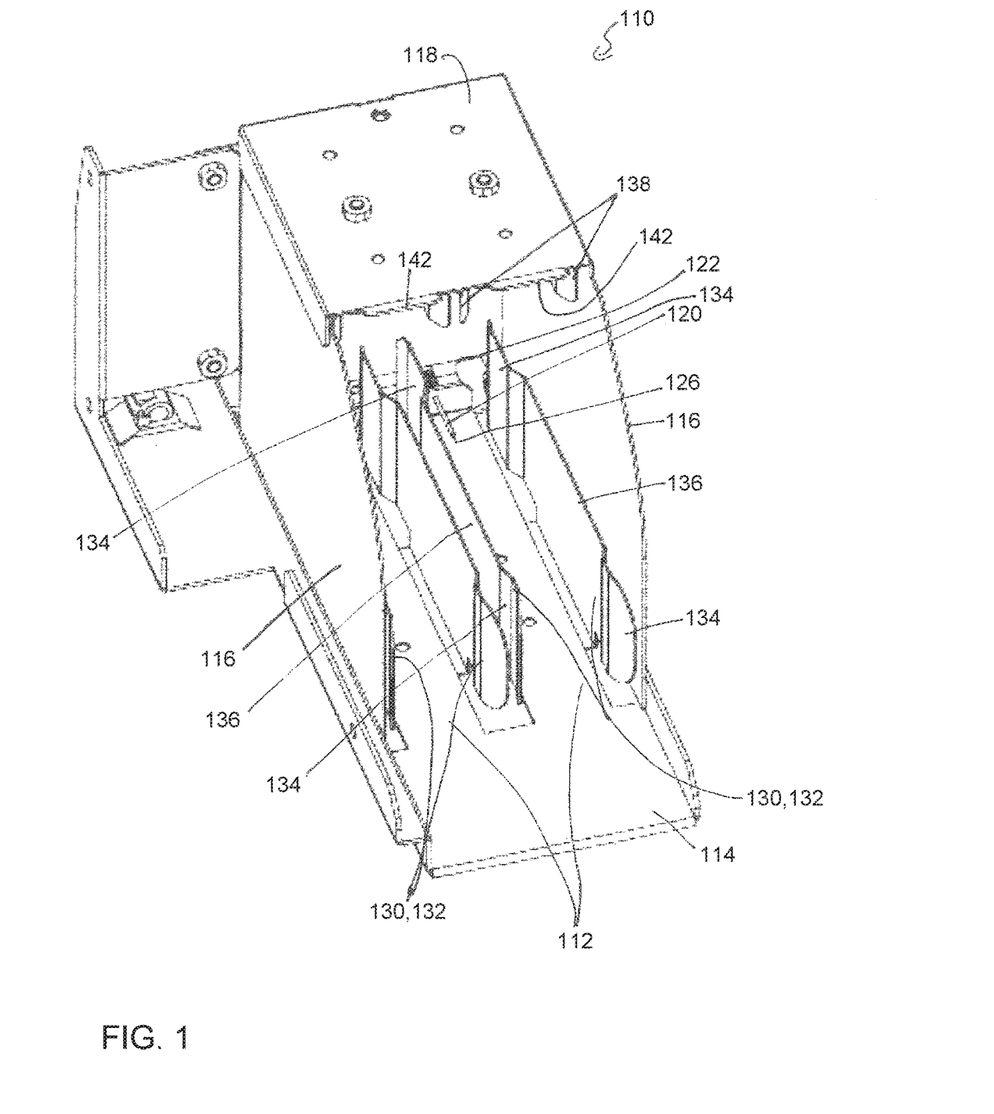
FIG. 1 illustrates a perspective view of a reagent vessel holder according to an embodiment of the present invention according to an embodiment of the present disclosure.

Referring initially to FIG. 1, FIG. 1 shows a perspective view of a reagent vessel holder 110. The reagent vessel holder 110 can comprise at least one reagent vessel compartment 112. According to the embodiment shown in FIG. 1, the reagent vessel holder 110 can comprise two reagent vessel compartments 112. It can be explicitly stated that the reagent vessel holder 110 may also comprise more than the two reagent vessel compartments 112. For example, the reagent vessel holder 110 may comprise a plurality of reagent vessel compartments 112. The reagent vessel compartments 112 can comprise a base 114, sidewalls 116 and a cover 118. The cover 118 can be disposed opposite to the base 114. The cover 118 and the base 114 can be connected to one another by the sidewalls 116. The reagent vessel compartments 112 may be made of metal such as a metal plate or metal sheet.

The reagent vessel holder 110 can further comprise at least one hollow needle 120. The hollow needle 120 may be made of a metal such as titanium. Needless to say, the hollow needle 120 may be made from any appropriate material such as stainless steel. The hollow needle 120 can be disposed on a front end 122 of the reagent vessel compartment 112 near the base 114. In one embodiment, two hollow needles 120 can be present, each of which can be disposed on the front end 122 of a reagent vessel compartment 112. It can be explicitly stated that the reagent vessel holder 110 may also comprise more than the two hollow needles 120. For example, if the reagent vessel holder 110 comprises a plurality of reagent vessel compartments 112, the reagent vessel holder 110 can comprise a plurality of hollow needles 120. Each of the plurality of hollow needles 120 can be disposed on the front end 122 of each of the plurality of reagent vessel compartments 112. The hollow needle 120 can extend in a direction substantially parallel to the base 114. The hollow needle 120 can project into the reagent vessel compartment 112. For example, the hollow needle 120 can comprise a longitudinal axis 124 which is substantially parallel to the base 114. The hollow needle 120 can comprise a conical leading end 126, which can be closed, and a lateral opening 128 for drawing in of a reagent fluid. The lateral opening 128 can be provided close behind the leading end 126.

The reagent vessel compartment 112 can comprise at least two lateral guiding elements 130. As shown in FIG. 1, the lateral guiding elements 120 can be disposed near the base 114. The lateral guiding elements 130 can be disposed substantially parallel to the direction in which the hollow needle 120 extends. In one embodiment, the lateral guiding elements 130 can be arranged symmetrically with respect to the direction in which the hollow needle 120 extends. For example, the lateral guiding elements 130 can be spaced apart from the longitudinal axis 124 with identical distances. The lateral guiding elements 130 can be biased towards one another. The lateral guiding elements 130 can comprise identical biasing forces. According to the embodiment shown in FIG. 1, the lateral guiding elements 130 can be plate springs 132. Each of the plate springs 132 can be formed so as to comprise two contacting elements 134 and a connecting portion 136 connecting the contacting elements 134. The connecting portions 136 can be recessed relative to the contacting elements 134 in a direction away from one another.

Figure 2:
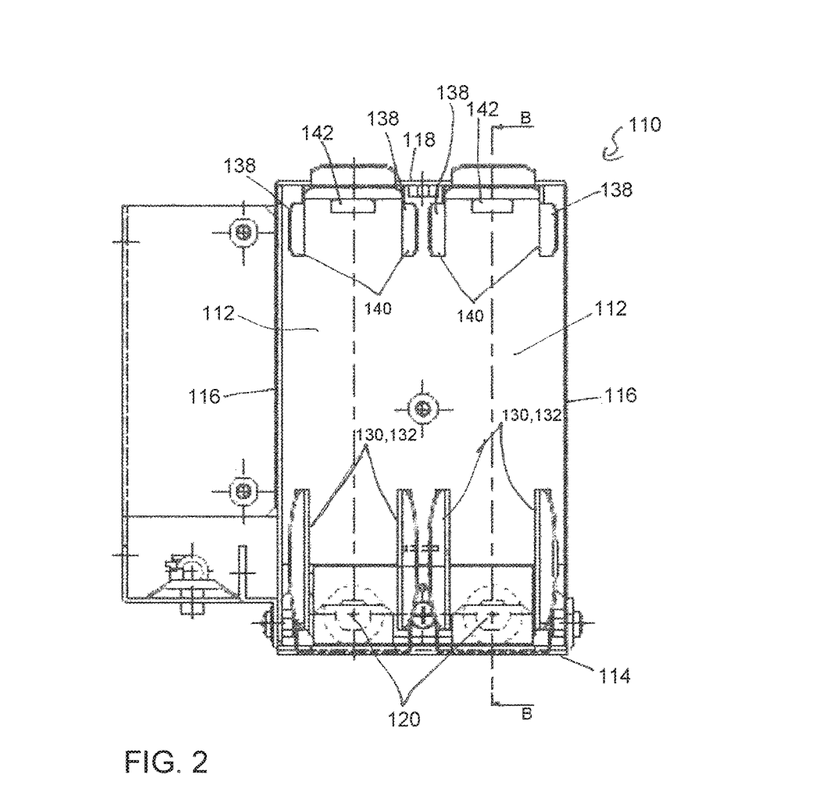
FIG. 2 illustrates a front view of the reagent vessel holder according to an embodiment of the present disclosure.

FIG. 2 shows a front view of the reagent vessel holder 110. As shown in FIG. 2, the reagent vessel compartment 112 can further comprise upper lateral guiding elements 138 which can be disposed substantially parallel to the direction in which the hollow needle 120 extends. The upper lateral guiding elements 138 can be disposed at a position away from the base 114. According to the embodiment shown in FIG. 2, the upper lateral guiding elements 138 can be disposed near the cover 118. The upper lateral guiding elements 138 may be stationary with respect to the cover 118. Each of the upper lateral guiding elements 138 may comprise an angled leading end 140. The angled leading ends 140 may be formed so as to converge in a direction parallel to the base and towards the hollow needle 120. The upper lateral guiding elements 138 may be made of plastics or metal.

The reagent vessel holder 110 can further comprise at least one upper guiding element 142 disposed at the cover 118 and substantially parallel to the direction in which the hollow needle 120 extends. Particularly, the upper guiding element 142 can be disposed in the center between the upper lateral guiding elements 138.

Figure 3:
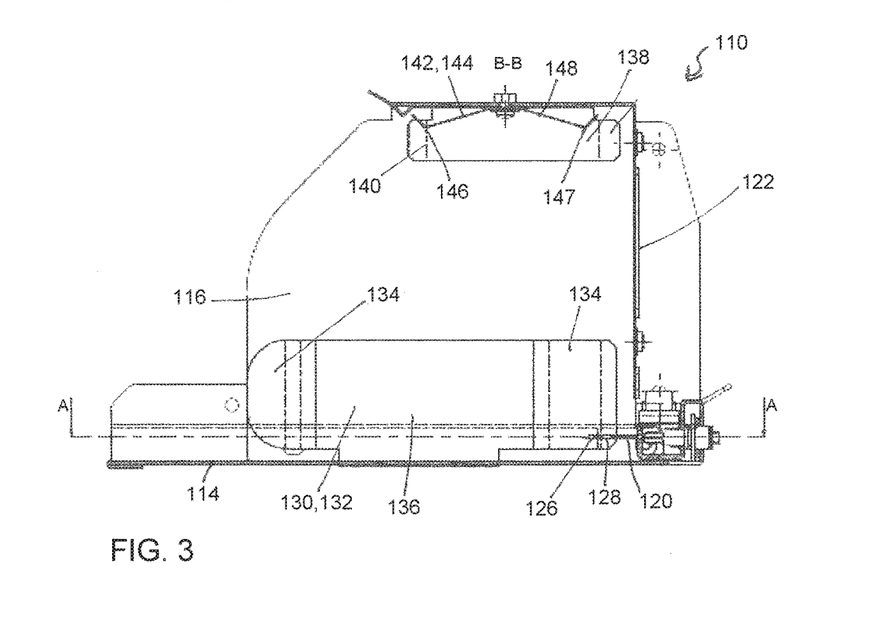
FIG. 3 illustrates a cross-sectional view taken along line B-B of FIG. 2 according to an embodiment of the present disclosure.

FIG. 3 shows a cross-sectional view taken along line B-B of FIG. 2. As shown in FIG. 3, the upper guiding element 142 can be a plate spring 144. The plate spring 144 can comprise at least one contacting element. In this embodiment, the plate spring 144 can comprise a first contacting element 146, a second contacting element 147 and a connecting portion 148 connecting the contacting elements 146, 147. The connecting portion 148 can be recessed relative to the contacting elements 146, 147 in a direction away from the base 114.

Figure 4:
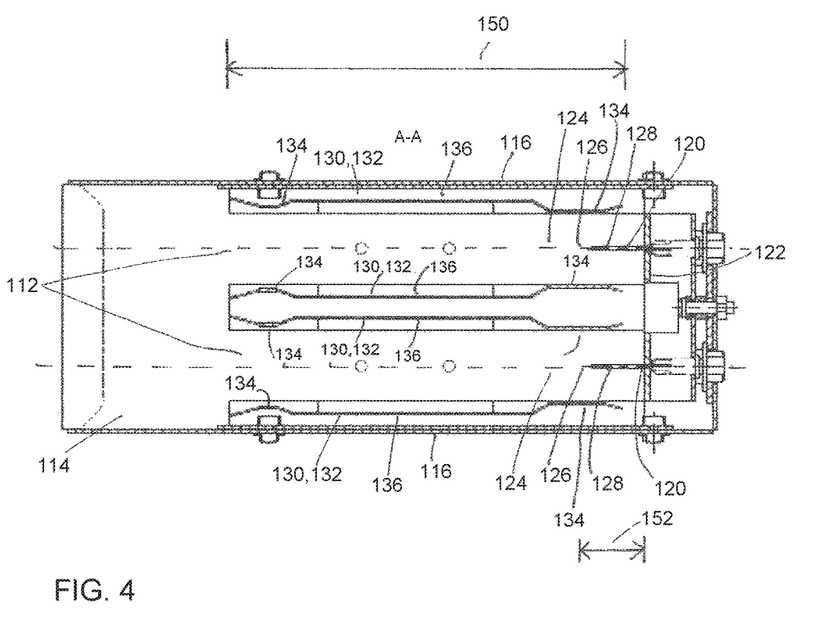
FIG. 4 illustrates a cross-sectional view taken along line A-A of FIG. 3 according to an embodiment of the present disclosure.

FIG. 4 shows a cross-sectional view along line A-A of FIG. 3. As shown in FIG. 4, the lateral guiding elements 130 can be formed so as to comprise a length 150 in a direction substantially parallel to the direction in which the hollow needle 120 extends. The length 150 can be greater than an effective length 152 of the hollow needle 120, i.e. a length by which the hollow needle 120 can project from the front end 122 into the reagent vessel compartment 112.

Figure 5:
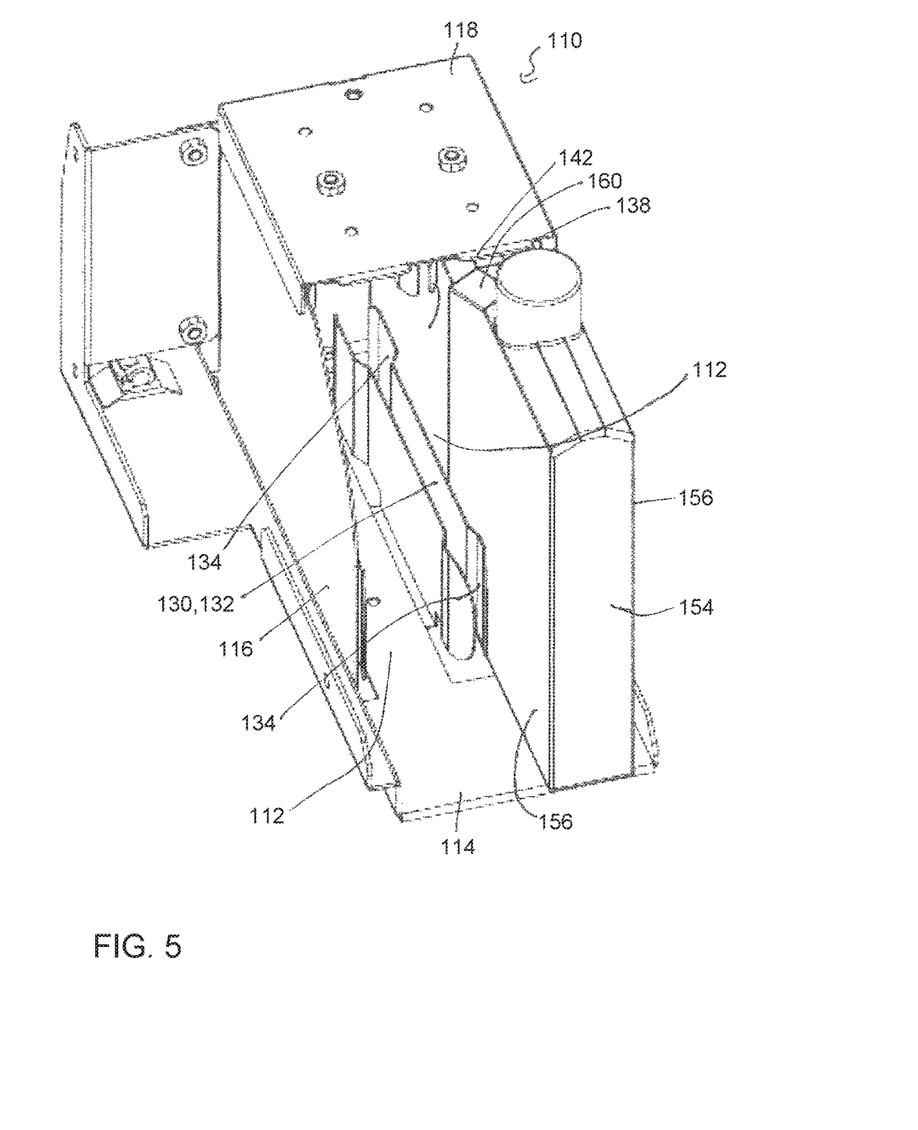
FIG. 5 illustrates a perspective view of the reagent vessel holder loaded with a reagent vessel according to an embodiment of the present disclosure.

FIG. 5 shows a perspective view of the reagent vessel holder 110 loaded with a reagent vessel 154. In one embodiment, the reagent vessel compartment 112 can be adapted to receive the reagent vessel 154. As shown in FIG. 5, the lateral guiding elements 130 can be adapted to receive the reagent vessel 154 therebetween. Similar, the upper lateral guiding elements 138 can be adapted to receive the reagent vessel 154 therebetween. As the lateral guiding elements 130 can comprise the two contacting elements 134 and can be biased to one another, the lateral guiding elements 130 can contact the reagent vessel 154 at two positions, which can be defined by the two contacting elements 134, on each side surface 156 of the reagent vessel 154 when the reagent vessel 154 is received by the lateral guiding elements 130. In one embodiment, the lateral guiding elements 130 can comprise biasing forces, which can be adjusted such that the lateral guiding elements 130 can be adapted to center the reagent vessel 154 when the reagent vessel 154 is received by the lateral guiding elements 130.

In order to load the reagent vessel holder 110 with the reagent vessel 154, the reagent vessel 154 can be supplied from an end of the reagent vessel compartment 112 opposite to the front end 122. Then the reagent vessel 154 can be moved between the lateral guiding elements 130 and pushed therethrough. The lateral guiding elements 130 can be adapted to slidably guide the reagent vessel 154 in a direction substantially parallel to the direction in which the hollow needle 120 extends. Similar, the upper lateral guiding elements 138 can be adapted to slidably guide the reagent vessel 154 in a direction substantially parallel to the direction in which the hollow needle 120 extends. The upper lateral guiding elements 138 can comprise a height set such that the reagent vessel 154 can be guided by them only at an upper portion, i.e. a portion of the reagent vessel 154 where the upper lateral guiding elements 138 may not contact any bulging of the reagent vessel 154 which otherwise might obstruct the loading process. Similar, the upper guiding element 142 can be adapted to slidably guide the reagent vessel 154 in a direction substantially parallel to the direction in which the hollow needle 120 extends. The reagent vessel 154 can be moved through the lateral guiding elements 130 until the hollow needle 120 pierces the reagent vessel 154 and the reagent vessel 154 can contact the front end 122 of the reagent vessel compartment 112.

Figure 6:
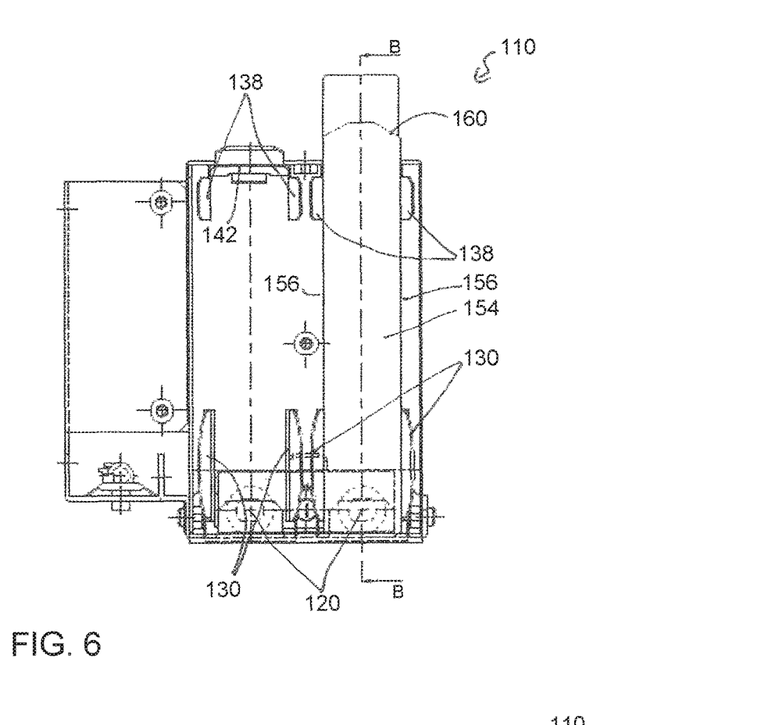
FIG. 6 illustrates a front view of the reagent vessel holder of FIG. 5 according to an embodiment of the present disclosure.

FIG. 6 shows a front view of the reagent vessel holder 110 of FIG. 5. Due to the biasing force of the lateral guiding elements 130, the reagent vessel 154 can be centered between the lateral guiding elements 130. As can be further taken from FIG. 6, the plate springs 132 can be formed so as to contact the reagent vessel 154 over a predetermined height 158. In one embodiment, the plate springs 132 can be formed so as to be elastically deformable to a different extent over the predetermined height 158. In other words, the plate springs 132 may pivot in a direction substantially perpendicular to the direction in which the hollow needle 120 extends.

Figure 7:
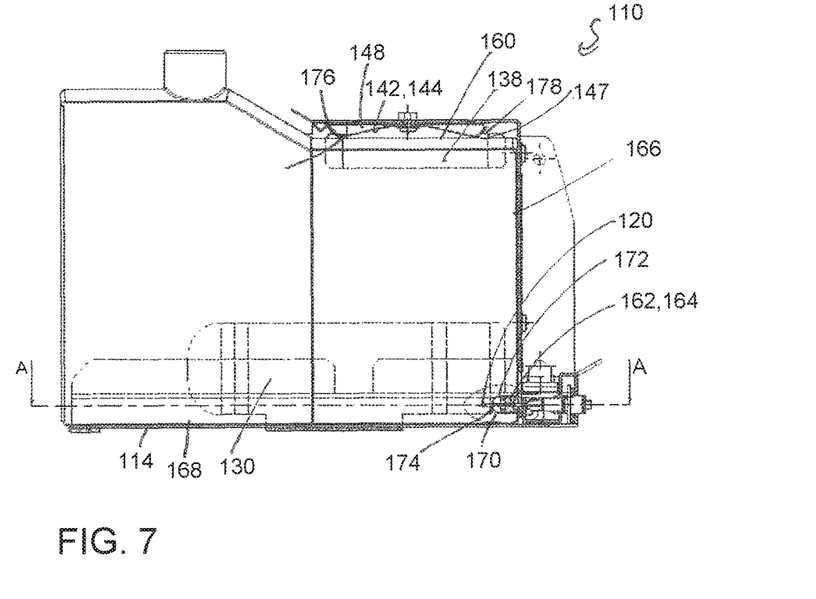
FIG. 7 illustrates a cross-sectional view taken along line B-B of FIG. 6 according to an embodiment of the present disclosure.

FIG. 7 shows a cross-sectional view taken along a line B-B of FIG. 6. The upper guiding element 142 can be adapted to contact the reagent vessel 154 at an upper surface 160 thereof. As the upper guiding element 142 can be a plate spring 144, which can comprise two contacting elements 146, 147, the upper guiding element 142 can contact the reagent vessel 154 at two positions of the upper surface 160 defined by the contacting elements 146, 147, as will be explained in more detail below.

The reagent vessel 154 can comprise a pierceable seal 162 including a pierceable elastomeric stopper 164 disposed in a front wall 166 of the reagent vessel 154. In one embodiment, the pierceable seal 162 can be disposed in the front wall 166 near a bottom 168 of the reagent vessel. For example, a blind hole 170 may be provided in the front wall as a socket for the pierceable elastomeric stopper 164. The blind hole 170 can comprise a cylindrical wall 172 and an end portion 174. In order to ensure a sufficiently large uniform wall thickness of the reagent vessel 154, it can be advantageous if, as shown, the end portion 174 is curved so as to have a dome shape which can be convex toward the interior of the reagent vessel 154, and has a smooth transitional region with the cylindrical wall 172 of the blind hole 170. The elastomeric stopper 164 may be covered with a sealing film, such as a pierceable foil, which in the area of the pierceable seal 162 can be fastened to the front wall 166 of the reagent vessel 154. In this way, the elastomeric stopper 164 can be protected from sliding out when the reagent vessel 154 is removed from the reagent vessel compartment 112. The sealing film can also form an additional seal for sealing the liquid in the reagent vessel 154.

FIG. 7 shows that the hollow needle 120 can be adapted to pierce the elastomeric stopper 164. The upper guiding element 142 can be adapted to contact the reagent vessel 154 at the upper surface 160 thereof when the reagent vessel 154 contacts the hollow needle 120 and before being pierced thereby. In one embodiment, the plate spring 144 can be formed so as to be adapted to contact the reagent vessel 154 at the upper surface 160 thereof at a first position 176 when the reagent vessel 154 contacts the hollow needle 120 and before being pierced thereby and to additionally contact the reagent vessel 154 at the upper surface 160 thereof at a second position 178 when the reagent vessel 154 is pierced by the hollow needle 120. The second position 178 can be closer to the hollow needle 120 than the first position 176. In other words, when moving the reagent vessel into the reagent vessel compartment 112, the reagent vessel 154 can first come into contact with the first contacting element 146, which can be disposed further away from the hollow needle 120, at the first position 176 and when moving further into the reagent vessel compartment 112 then comes into contact with the second contacting element 147, which can be disposed closer to the hollow needle 120, at the second position 178. Thus, the reagent vessel 154 can be reliably pressed downwards by the upper guiding element 142. Further, the plate spring 144 can press the reagent vessel 154 downwards along the complete length by which the hollow needle 120 is inserted into the reagent vessel 154.

In one embodiment, the lateral guiding elements 130 can serve to center the reagent vessel 154 therebetween in a horizontal direction, i.e. direction parallel to the base 114, and the upper guiding element 142 can press the reagent vessel 154 in a vertical direction towards the base 114. Thus, the hollow needle 120 can pierce the pierceable seal 162 in a center area of the elastomeric stopper 164. In one embodiment, the longitudinal axis 124 of the hollow needle 120 can extend through a middle point of the elastomeric stopper 164.

Figure 8:
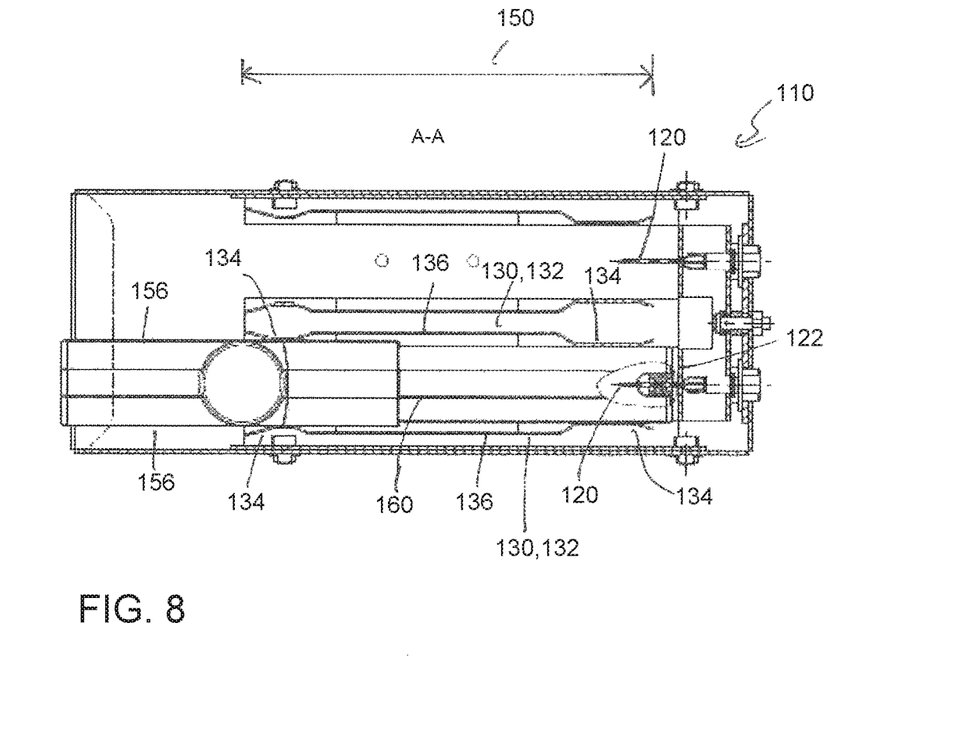
FIG. 8 illustrates a cross-sectional view taken along line A-A of FIG. 7 according to an embodiment of the present disclosure.

FIG. 8 shows a cross-sectional view taken along line A-A of FIG. 7. FIG. 8 shows how the lateral guiding elements 130 can contact the reagent vessel 154. This contacting of the lateral guiding elements 130 with the reagent vessel 154 can serve to compensate any tolerances concerning the width of the reagent vessel 154. In one embodiment, reagent vessels 154 may bulge such that the width may differ from reagent vessel to reagent vessel. The lateral guiding elements 130 can serve to center the reagent vessel 154 relative to the hollow needle 120 independent of the width thereof. In one embodiment, the biasing forces of the lateral guiding elements 130 can be adjusted so that reagent vessels 154 having a small width can reliably be contacted by the lateral guiding elements 130 and that reagent vessels 140 having a great width may still be introduced between the lateral guiding elements 130 without excessive force. As the lateral guiding elements may be elastically deformed to a different extent over the height 158 of the reagent vessel 154, even a bulging can be compensated in vertical direction, i.e. a direction substantially perpendicular to the base 114. As the connection portion 136 can be recessed relative to the contacting portions 134, a bulging in horizontal direction, i.e. a direction substantially parallel to the base 114, can be compensated.

The reagent vessel holder 110 may be part of a reagent supply system which can comprise at least one reagent vessel 154 held by the reagent vessel compartment 112 of the reagent vessel holder 110. The reagent supply system may be used in cooperation with an analytical instrument such as a medical analytical instrument. The analytical instrument can comprise a reagent space for accommodating the reagent supply system and a reagent communication system for communicating fluid from the reagent vessel 154. The reagent communication system can comprise a connection adapted to be connected to the hollow needle 120 of the reagent vessel holder 110 for establishing fluid communication with an interior of the reagent vessel 154 such that a reagent contained in the reagent vessel 154 can be withdrawable by the reagent communication system.

The reagent vessel holder 110 may be modified. The lateral guiding elements 130 may comprise contacting elements which are at least partially spherical. For example, the lateral guiding elements 130 can comprise contacting elements which can be substantially hemispherical. The reagent vessel holder 110 may further comprise a needle holder for holding the hollow needle 120 in a stationary position with respect to the reagent vessel compartment 112. The needle holder and the lateral guiding elements 130 may be integrally formed in this case. This can provide advantages in that any tolerances concerning the mounting position between the needle holder of the hollow needle 120 and the guiding elements and the adjusting may be avoided.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A reagent vessel holder for an analytical instrument, the reagent vessel holder comprising:
    at least one reagent vessel compartment for receiving a reagent vessel comprising a pierceable seal disposed in a front wall near a bottom of the reagent vessel, wherein the at least one reagent vessel compartment comprises a base, a pair of lower lateral guiding elements, and a pair of upper lateral guiding elements; and
    at least one hollow needle for piercing the reagent vessel, wherein the hollow needle is disposed on a front end of the at least one reagent vessel compartment near the base and extends in a direction substantially parallel with a deviation of less than 15° to the base, wherein each pair of lateral guiding elements is disposed so as to be adapted to slidably guide the reagent vessel in a direction substantially parallel to the direction in which the hollow needle extends, wherein the lateral guiding elements of each pair are adapted to receive the reagent vessel therebetween and are biased towards one another, wherein the lateral guiding elements are plate springs, wherein each of the plate springs is formed so as to comprise two contacting elements for contacting the reagent vessel at two positions and a connecting portion connecting the contacting elements, and wherein the connecting portions are recessed relative to the contacting elements in a direction away from one another.

2. The reagent vessel holder according to claim 1, wherein the lower lateral guiding elements are disposed near the base.

3. The reagent vessel holder according to claim 1, wherein the lateral guiding elements comprise biasing forces, which are adjusted such that the lateral guiding elements are adapted to center the reagent vessel when the reagent vessel is received by the lateral guiding elements.

4. The reagent vessel holder according to claim 1, wherein the plate springs are adapted to pivot in a direction perpendicular to the direction in which the hollow needle extends, so as to be elastically deformable to a different extent over a predetermined height.

5. The reagent vessel holder according to claim 1, wherein the at least one reagent vessel compartment further comprises a cover disposed at an end of the at least one reagent vessel compartment opposite to the base and at least one upper guiding element disposed at the cover so as to be adapted to slidably guide the reagent vessel in a direction substantially parallel to the direction in which the hollow needle extends, wherein the at least one upper guiding element is adapted to contact the reagent vessel at an upper surface thereof.

6. The reagent vessel holder according to claim 5, wherein the at least one upper guiding element is adapted to contact the reagent vessel at the upper surface thereof when the reagent vessel contacts the hollow needle and before being pierced thereby.

7. The reagent vessel holder according to claim 5, wherein the at least one upper guiding element is a plate spring.

8. The reagent vessel holder according to claim 7, wherein the plate spring of the at least one upper guiding element is formed so as to be adapted to contact the reagent vessel at the upper surface thereof at a first position when the reagent vessel contacts the hollow needle and before being pierced thereby and to additionally contact the reagent vessel at the upper surface thereof at a second position when the reagent vessel is pierced by the hollow needle.

9. The reagent vessel holder according to claim 1, further comprising,
    a plurality of reagent vessel compartments for receiving a plurality of reagent vessels; and
    a plurality of hollow needles, wherein each of the plurality of hollow needles is disposed on a front end of each of the plurality of reagent vessel compartments.

10. A reagent supply system for an analytical instrument, the reagent supply system comprising:
    a reagent vessel holder according to claim 1; and
    a reagent vessel held by a reagent vessel compartment of the reagent vessel holder, wherein the reagent vessel comprises a pierceable seal in a front wall thereof adapted to be pierced by the hollow needle.

11. An analytical instrument, the analytical instrument comprising a reagent space accommodating a reagent supply system according to claim 10; and a reagent communication system for communicating fluid from the reagent vessel, wherein the reagent communication system comprises a connection adapted to be connected to the hollow needle of the reagent vessel holder for establishing fluid communication with an interior of the reagent vessel such that a reagent contained in the reagent vessel is withdrawable by the reagent communication system.

\* \* \* \* \*